(12) United States Patent
Itoh

(10) Patent No.: US 7,425,305 B2
(45) Date of Patent: Sep. 16, 2008

(54) SPECIMEN DISPENSING SYSTEM

(76) Inventor: Teruaki Itoh, 5-25, Kokaihommachi, Kumamoto-shi, Kumamoto-ken (JP)

( * ) Notice: Subject to any disclaimer, the term of this patent is extended or adjusted under 35 U.S.C. 154(b) by 611 days.

(21) Appl. No.: 10/715,391

(22) Filed: Nov. 19, 2003

(65) Prior Publication Data

US 2004/0105785 A1  Jun. 3, 2004

(30) Foreign Application Priority Data

Nov. 29, 2002 (JP) ............................. 2002-347584

(51) Int. Cl.
*G01N 21/13* (2006.01)
*B01L 3/02* (2006.01)

(52) U.S. Cl. .................. 422/65; 422/66; 422/63; 422/64; 422/67; 422/68.1; 422/100; 436/180

(58) Field of Classification Search ............ 422/65–66, 422/63–64, 100, 67, 68.1; 436/180
See application file for complete search history.

(56) References Cited

U.S. PATENT DOCUMENTS

| | | | | |
|---|---|---|---|---|
| 3,985,508 A | * | 10/1976 | Williams | 422/65 |
| 4,861,553 A | * | 8/1989 | Mawhirt et al. | 422/65 |
| 5,008,082 A | * | 4/1991 | Shaw | 422/65 |
| 5,158,895 A | * | 10/1992 | Ashihara et al. | 436/526 |
| 5,207,986 A | * | 5/1993 | Kadota et al. | 422/65 |
| 5,576,214 A | * | 11/1996 | Shaw | 436/43 |
| 5,985,214 A | * | 11/1999 | Stylli et al. | 422/65 |
| 6,019,945 A | * | 2/2000 | Ohishi et al. | 422/65 |
| 6,261,521 B1 | * | 7/2001 | Mimura et al. | 422/67 |
| 6,358,471 B1 | * | 3/2002 | Ishihara | 422/65 |
| 6,444,171 B1 | * | 9/2002 | Sakazume et al. | 422/65 |
| 6,461,570 B2 | * | 10/2002 | Ishihara et al. | 422/65 |
| 6,495,369 B1 | * | 12/2002 | Kercso et al. | 436/47 |
| 6,599,476 B1 | * | 7/2003 | Watson et al. | 422/63 |
| 6,627,446 B1 | * | 9/2003 | Roach et al. | 436/43 |
| 6,866,820 B1 | * | 3/2005 | Otto et al. | 422/63 |
| 6,916,447 B2 | * | 7/2005 | Kowallis | 422/66 |
| 6,936,474 B2 | * | 8/2005 | Chiou et al. | 436/180 |
| 7,028,831 B2 | * | 4/2006 | Veiner | 198/619 |
| 2003/0086824 A1 | * | 5/2003 | Sasaki et al. | 422/82.09 |

FOREIGN PATENT DOCUMENTS

| | | |
|---|---|---|
| JP | 10-227800 | 8/1998 |
| JP | 2000-193670 | 7/2000 |

* cited by examiner

*Primary Examiner*—Brian R. Gordon
(74) *Attorney, Agent, or Firm*—Nixon & Vanderhye P.C.

(57) ABSTRACT

A specimen dispensing system includes a conveying mechanism for conveying a master specimen container containing a specimen and a required number of empty slave specimen containers on a conveyor lane, the master and slave specimen containers being aligned in a conveyance direction. A stopping mechanism temporarily stops the master and slave specimen containers when the master and slave specimen containers reach a position under a dispensing nozzle in a dispensing unit. The dispensing unit removes the specimen from the master specimen container by the dispensing nozzle when the master specimen container is temporarily stopped in the position under the dispensing nozzle and dispenses the specimen to the slave specimen containers when the slave specimen containers are temporarily stopped in the position under the dispensing nozzle.

2 Claims, 2 Drawing Sheets

SPECIMEN DISPENSING SYSTEM

CROSS-REFERENCE TO RELATED APPLICATIONS

This application is based upon and claims the benefit of priority from the prior Japanese Patent Application No. 2002-347584, filed Nov. 29, 2002, the entire contents of which are incorporated herein by reference.

BACKGROUND OF THE INVENTION

1. Field of the Invention

The present invention relates to a specimen dispensing system for dispensing specimens such as blood and urine.

2. Description of the Related Art

Jpn. Pat. Appln. KOKAI Publication No. 10-227800 discloses a prior art specimen dispensing system. This system is so configured that a specimen in a specimen container on a master line is dispensed to its corresponding specimen containers on a plurality of (two) slave lines by a plurality of (two) nozzles.

FIGS. 3 and 4 illustrate a specimen dispensing system that is substantially the same as the above prior art system. The system shown in FIGS. 3 and 4 includes first to sixth conveyor lanes 1 to 6. The first to third conveyor lanes 1 to 3 convey master specimen containers 11 to 13 and the fourth to sixth conveyor lanes 4 to 6 convey slave specimen containers 21 to 23. Master specimens are removed from the master specimen containers 11 to 13 and dispensed to the slave specimen containers 21 to 23, which are empty, using first to third dispensing nozzles N1 to N3, respectively.

After the dispensing, the master specimen containers 11 to 13 are returned by a return lane 7. The slave specimen containers 21 to 23 are returned by a return lane 8. In FIGS. 3 and 4, reference symbol La indicates a dispensing tip mounting position and reference symbol Lb indicates a dispensing tip discarding position. The first to third dispensing nozzles N1 to N3 can be moved in a direction crossing the conveyor lanes (right and left directions in FIGS. 3 and 4) by a dispensing nozzle moving mechanism S (see FIG. 4) that is controlled by a controller (not shown). In FIG. 3, NP1 to NP3 represent moving positions of the first to third dispensing nozzles N1 to N3, respectively.

Pay attention to the movement of, for example, the first dispensing nozzle N1 in the above dispensing operation. Referring to FIG. 4, the nozzle N1 discards a used dispensing tip Tb in the dispensing tip discarding position Lb and mounts a new dispensing tip Ta in the dispensing tip mounting position La. After that, the nozzle N1 moves to the first conveyor lane 1 and removes a master specimen from the master specimen container 11. The nozzle N1 moves to the position of the empty slave specimen container 21 on the fourth conveyor lane 4 and dispenses the master specimen to the container 21. Then, the nozzle N1 returns to the original position. The second and third dispensing nozzles N2 and N3 perform the same operation.

The above prior art specimen dispensing system causes the following disadvantage if the dispensing nozzles N1 to N3 are quickly moved in order to perform a dispensing operation at high speed. When the dispensing nozzles N1 to N3 move beyond a fixed speed, the removed specimens are likely to be scattered due to a shock caused when the nozzles are stopped, though there are differences in the shape and size of dispensing tips mounted on the nozzles N1 to N3 and the type of specimens. If the specimens are scattered, not only will they decrease in amount but also a so-called contamination occurs, thus causing serious problems.

In order to avoid the above problems, each of the dispensing nozzles restricts its moving speed by itself. The nozzles therefore decrease in throughput. To provide a number of dispensing nozzles, however, increases the size of the system.

BRIEF SUMMARY OF THE INVENTION

An object of the present invention is to provide a specimen dispensing system having the following advantages.

The time required for moving a dispensing nozzle can greatly be shortened.

It is unlikely that no specimens will be scattered even though a dispensing nozzle moves at high speed.

The size of the specimen dispensing system is small but the throughput thereof is large.

In order to attain the above object, a specimen dispensing system according to the present invention has the following characteristic configuration. The other characteristic configurations will be clarified in the embodiment.

A specimen dispensing system according to an embodiment of the present invention comprises:

conveying means for conveying a master specimen container containing a specimen and a required number of empty slave specimen containers on a conveyor lane, the master and slave specimen containers being aligned in a conveyance direction;

stopping means for temporarily stopping the master and slave specimen containers when the master and slave specimen containers reach a position under a dispensing nozzle in a dispensing unit; and dispensing means for removing the specimen from the master specimen container by the dispensing nozzle when the master specimen container is temporarily stopped in the position under the dispensing nozzle by the stopping means and dispensing the specimen to the slave specimen containers when the slave specimen containers are temporarily stopped in the position under the dispensing nozzle.

DETAILED DESCRIPTION OF THE INVENTION (Embodiment)

Figure 1:
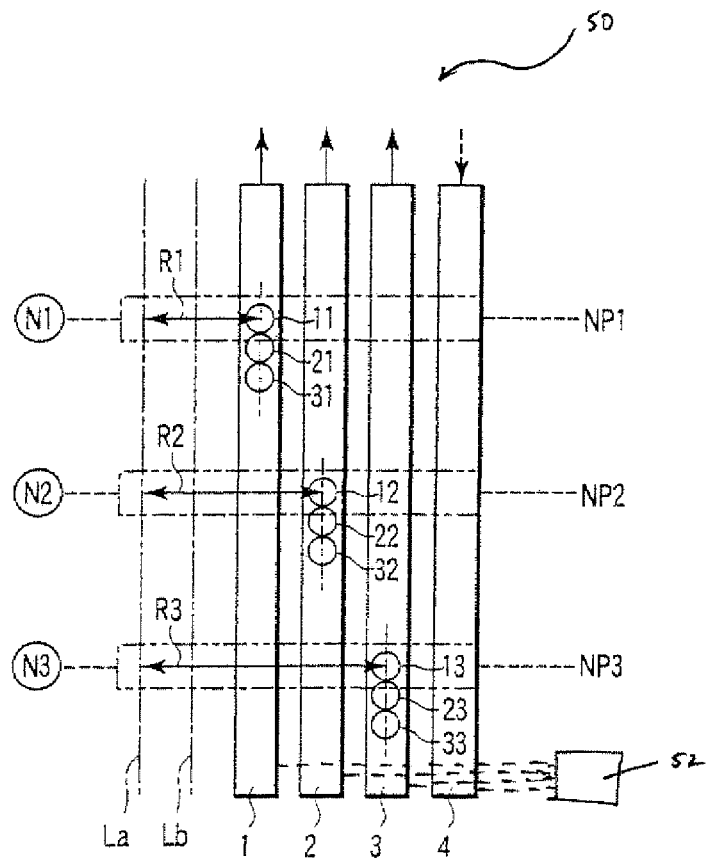
FIG. 1 is a schematic plan view of a specimen dispensing system according to an embodiment of the present invention.
Figure 2:
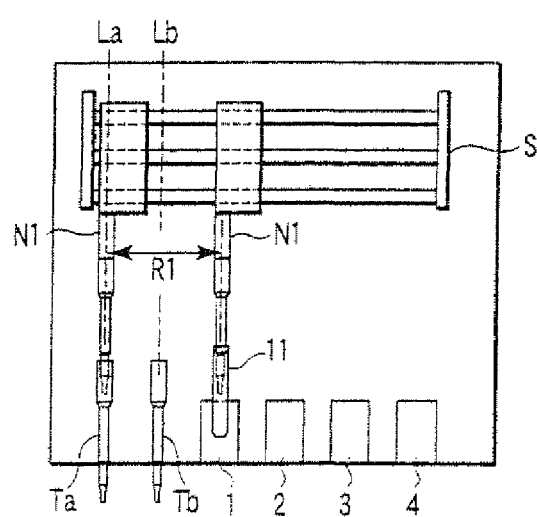
FIG. 2 is an illustration explaining the movement of a first dispensing nozzle of the specimen dispensing system according to an embodiment of the present invention.
Figure 3:
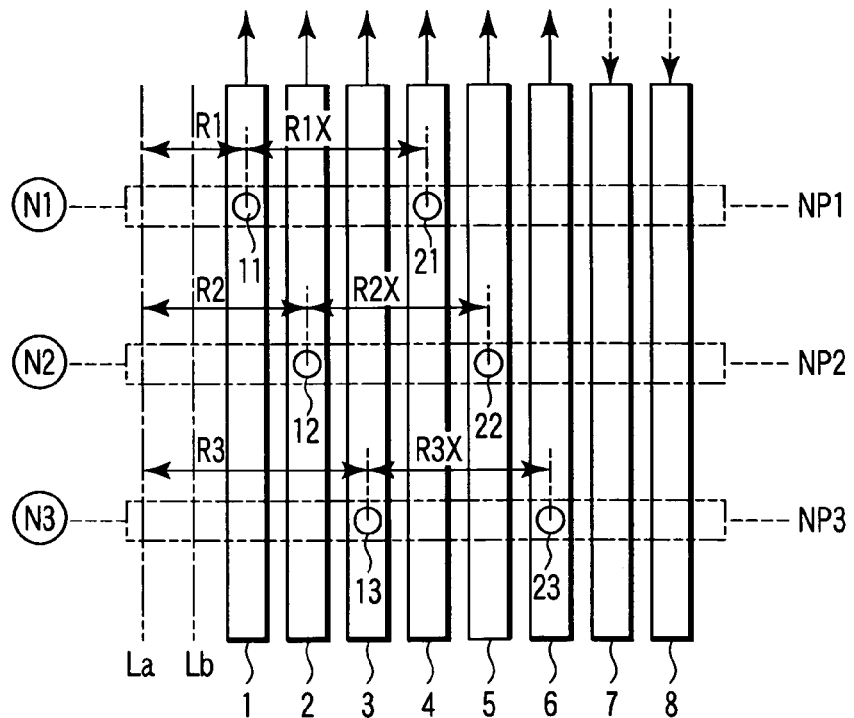
FIG. 3 is a schematic plan view showing a configuration of a prior art specimen dispensing system.
Figure 4:
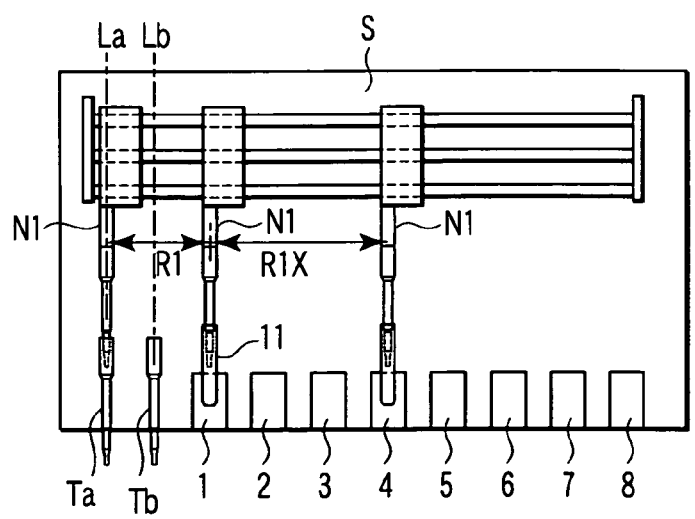
FIG. 4 is an illustration explaining the movement of a first dispensing nozzle of the prior art specimen dispensing system.

FIGS. 1 and 2 illustrate a specimen dispensing system according to an embodiment of the present invention. The system includes first, second and third conveyor lanes 1, 2 and 3. A conveying means (shown schematically via arrows 50) conveys a master specimen container 11 containing a specimen and a required number of empty slave specimen containers 21 and 31 on the first conveyor lane 1. The conveying means is capable of conveying the containers with known structure, similar to that of the prior art. Further details thereof are omitted. The conveying means conveys a master specimen container 12 containing a specimen and a required number of empty slave specimen containers 22 and 32 on the second conveyor lane 2. It conveys a master specimen container 13 containing a specimen and a required number of empty slave specimen containers 23 and 33 on the third conveyor lane 3. The master and slave specimen containers are aligned in the conveyance direction on their respective lanes.

When the master specimen container 11 and empty slave specimen containers 21 and 31 on the first conveyor lane 1 reach a position under a first dispensing nozzle N1 in a dispensing unit, they are stopped by a stopping means 52 (shown schematically in FIG. 1).

When the master specimen container 12 and empty slave specimen containers 22 and 32 on the second conveyor lane 2 reach a position under a second dispensing nozzle N2 in the dispensing unit, they are stopped by the stopping means 52.

When the master specimen container 13 and empty slave specimen containers 23 and 33 on the third conveyor lane 3 reach a position under a third dispensing nozzle N3 in the dispensing unit, they are stopped by the stopping means 52.

The first to third dispensing nozzles N1 to N3 are moved in a direction crossing the conveyor lanes (right and left directions in FIGS. 1 and 2) by a dispensing nozzle moving mechanism S that is controlled by a controller (not shown). In FIG. 1, NP1 to NP3 indicate moving positions of the first to third dispensing nozzles N1 to N3, respectively.

When the master specimen containers 11, 12 and 13 stop in positions under the dispensing nozzles N1, N2 and N3, the nozzles N1, N2 and N3 remove specimens from the master specimen containers 11, 12 and 13, respectively.

When the slave specimen container 21 temporarily stops in a position on the first conveyor lane 1 under the first dispensing nozzle N1, the specimen is dispensed to the slave specimen container 21 from the first dispensing nozzle N1. Similarly, when the slave specimen container 31 temporarily stops in a position on the first conveyor lane 1 under the first dispensing nozzle N1, the specimen is dispensed to the slave specimen container 31 from the first dispensing nozzle N1.

When the slave specimen container 22 temporarily stops in a position on the second conveyor lane 2 under the second dispensing nozzle N2, the specimen is dispensed to the slave specimen container 22 from the second dispensing nozzle N2. Similarly, when the slave specimen container 32 temporarily stops in a position on the second conveyor lane 2 under the second dispensing nozzle N2, the specimen is dispensed to the slave specimen container 32 from the second dispensing nozzle N2.

When the slave specimen container 23 temporarily stops in a position on the third conveyor lane 3 under the third dispensing nozzle N3, the specimen is dispensed to the slave specimen container 23 from the third dispensing nozzle N3. Similarly, when the slave specimen container 33 temporarily stops in a position on the third conveyor lane 3 under the third dispensing nozzle N3, the specimen is dispensed to the slave specimen container 33 from the third dispensing nozzle N3.

After the dispensing, the master specimen containers 11 to 13 and slave specimen containers 21 to 23 and 31 to 33 are all returned by a return lane 4. In FIGS. 1 and 2, reference symbol La indicates a dispensing tip mounting position and reference symbol Lb indicates a dispensing tip discarding position.

Pay attention to the movement of, for example, the first dispensing nozzle N1 in the above dispensing operation. Referring to FIG. 2, the first dispensing nozzle N1 discards a used dispensing tip Tb in the dispensing tip discarding position Lb and mounts a new dispensing tip Ta in the dispensing tip mounting position La. After that, the nozzle N1 moves onto the first conveyor lane 1 and removes a master specimen from the master specimen container 11. The nozzle N1 stands still in this position afterward. When the slave specimen container 21 moves on the first conveyor lane 1 and stops in a position under the first dispensing nozzle N1, the nozzle N1 dispenses the specimen to the specimen container 21. Similarly, when the slave specimen container 31 moves on the first conveyor lane 1 and stops in a position under the first dispensing nozzle N1, the nozzle N1 dispenses the specimen to the specimen container 31. When the above dispensing operation is completed, the first dispensing nozzle N1 returns to the original position.

The moving range in which the first dispensing nozzle N1 moves for its dispensing operation is only the one indicated by arrow R1. Comparing the moving range with the moving range (R1+R1X) of the first dispensing nozzle N1 of the prior art system, the conventionally-required moving range R1X becomes unnecessary. The moving range R1 is one in which a dispensing tip containing almost no specimen moves. In other words, the moving range R1 corresponds to the sum of a process performed until a new tip Ta is mounted on the first dispensing nozzle N1 in the stage prior to the dispensing of a master specimen and a process performed until the used dispensing tip Tb is discarded in the dispensing tip discarding position Lb after the specimen is dispensed to the slave specimen container.

The second and third dispensing nozzles N2 and N3 perform the same operation as described above.

(Features of the Embodiment)

[1] A specimen dispensing system according to an embodiment, comprises:

conveying means for conveying a master specimen container 11 containing a specimen and a required number of empty slave specimen containers 21 and 31 on a conveyor lane 1, the master and slave specimen containers being aligned in a conveyance direction;

stopping means for temporarily stopping the master and slave specimen containers 11, 21 and 31 when the master and slave specimen containers 11, 21 and 31 reach a position under a dispensing nozzle N1 in a dispensing unit; and dispensing means for removing the specimen from the master specimen container 11 by the dispensing nozzle N1 when the master specimen container 11 is temporarily stopped in the position under the dispensing nozzle N1 by the stopping means and dispensing the specimen to the slave specimen containers 21 and 31 when the slave specimen containers 21 and 31 are temporally stopped in the position under the dispensing nozzle N1.

According to the above specimen dispensing system, the moving range R1 in which the dispensing nozzle N1 moves for its dispensing operation is reduced more than the moving range (R1+R1X) of the prior art system by the range indicated by arrow R1X. Consequently, the moving time of the nozzle in the range R1X becomes zero and is therefore shortened. The total width of the conveyor lanes is about ½ that of the conveyor lanes of the prior art system. The moving range R1 is one in which a dispensing tip containing almost no specimen moves. It is thus unlikely that the specimen will be scattered even though the dispensing nozzle N1 moves at high speed. Since, moreover, the moving time of the nozzle N1 is shortened and the moving speed thereof is enhanced, its throughput can be enhanced without increasing the number of dispensing nozzles. Thus, the specimen dispensing system of the present invention can be decreased in size but increased in throughput.

[2] In the specimen dispensing system according to above item [1], the specimen is dispensed to the slave specimen containers 21 and 31 from the master specimen container 11 on the conveyor lane 1 concurrently with dispensing operations on other conveyor lanes 2, 3.

What is claimed is:

1. A specimen dispensing system comprising:
    a master specimen container containing a specimen;
    a required number of empty slave specimen containers;
    a plurality of conveyor lanes;
    conveying means cooperable with the conveyor lanes for conveying the master specimen container and the empty slave specimen containers on the plurality of conveyor lanes, wherein the master and slave specimen containers are aligned on the conveyor lanes in a conveyance direction;
    a dispensing means including a dispensing nozzle; and
    stopping means for temporarily stopping the master and slave specimen containers when the master and slave specimen containers reach a position under the dispensing nozzle,
    said dispensing means for removing the specimen from the master specimen container by the dispensing nozzle when the master specimen container is temporarily stopped in the position under the dispensing nozzle and dispensing the specimen to the slave specimen containers when the slave specimen containers are temporarily stopped in the position under the dispensing nozzle, wherein a controller moves the dispensing nozzle in a direction crossing the conveyor lanes.

2. The specimen dispensing system according to claim 1, further comprising a plurality of said dispensing nozzles, wherein each of the dispensing nozzles dispenses the specimen to the slave specimen containers from the master specimen container on the conveyor lane concurrently with dispensing operations on other conveyor lanes.

* * * * *